United States Patent [19]

Mensink et al.

[11] 4,015,609
[45] Apr. 5, 1977

[54] CIRCUIT FOR LOW POWER-LOW ENERGY SOURCE

[75] Inventors: Cor A. Mensink, Voorst; Jan P. Schuimer, Dieren, both of Netherlands

[73] Assignee: Vitatron Medical B.V., Dieren, Netherlands

[22] Filed: Nov. 17, 1975

[21] Appl. No.: 632,280

[52] U.S. Cl. .............. 128/419 PG; 128/419 PS; 307/251; 321/2; 323/DIG. 1; 331/112

[51] Int. Cl.² .................. A61N 1/36; H02M 3/335

[58] Field of Search ............ 321/2, 44; 323/22 R, 323/DIG. 1; 307/240, 251; 128/419 PG, 419 PS; 331/111, 112

[56] References Cited

UNITED STATES PATENTS

| | | | |
|---|---|---|---|
| 3,522,519 | 8/1970 | Petersen | 307/251 |
| 3,551,693 | 12/1970 | Burns et al. | 307/251 |
| 3,681,674 | 8/1972 | Terry | 321/2 |
| 3,818,304 | 6/1974 | Hursen et al. | 321/2 |
| 3,824,450 | 7/1974 | Johnson et al. | 321/2 |

Primary Examiner—William H. Beha, Jr.
Attorney, Agent, or Firm—Woodcock, Washburn, Kurtz & Mackiewicz

[57] ABSTRACT

A DC to DC converter with voltage regulator for converting a low level voltage source to a higher level DC, comprising an oscillator circuit with a low resistance starting current path, a rectifier circuit for rectifying the oscillator output, and a regulator for providing a regulated DC output voltage of predetermined level. The oscillator embodies one or more FET devices connected to provide an extremely low DC startup resistance as well as a low cutoff voltage characteristic. With this configuration, the low startup current from the voltage source can initiate switching so that oscillation can occur.

22 Claims, 2 Drawing Figures

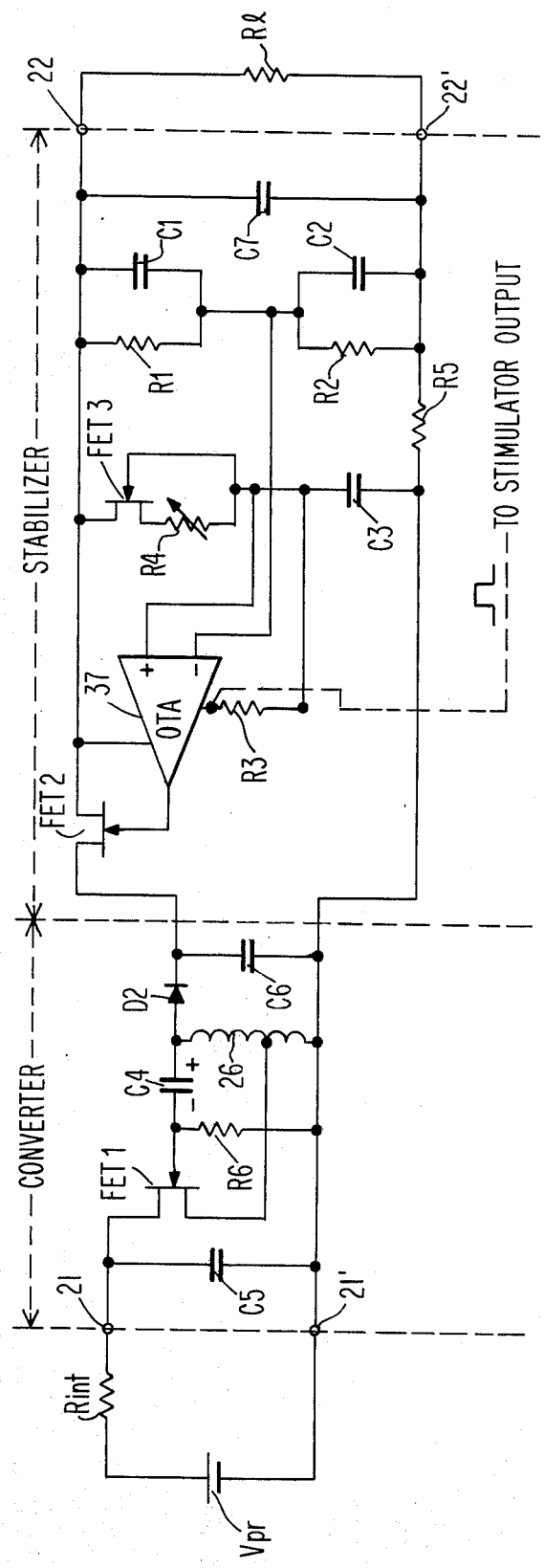
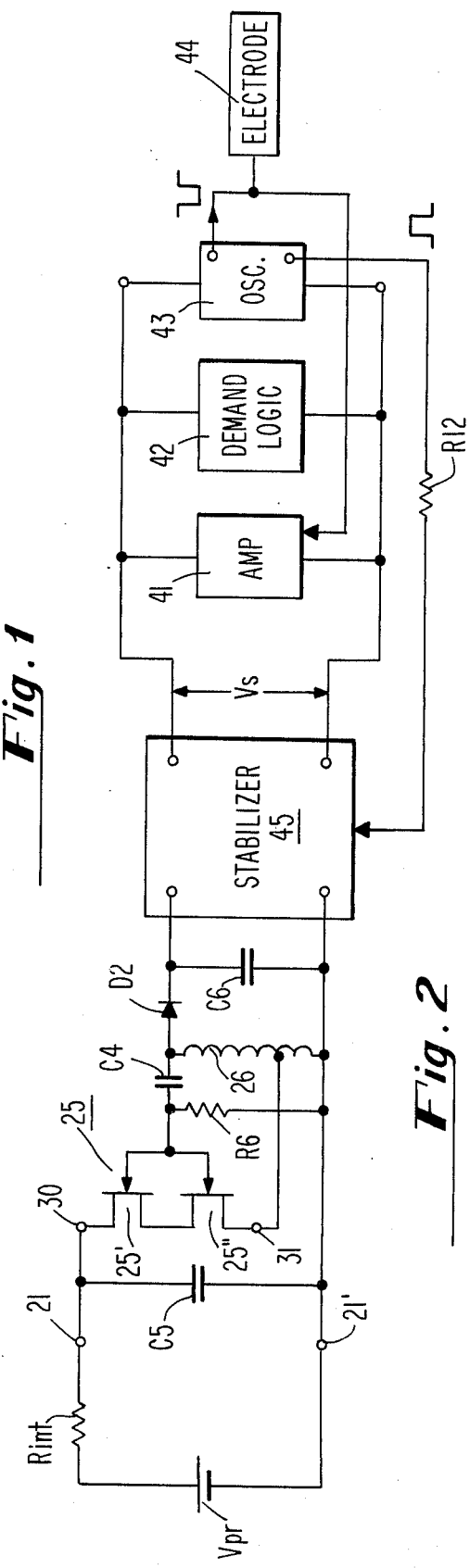
Fig. 1
Fig. 2

CIRCUIT FOR LOW POWER-LOW ENERGY SOURCE

BACKGROUND OF THE INVENTION

1. Field of the Invention

This invention lies in the area of DC to DC converter devices and, more particularly, converter devices adapted to provide efficient low power drain conversion of extremely low level DC power sources.

2. Description of the Prior Art

DC to DC converters have been widely used in the prior art for conversion of a low level source to a higher level DC source. Generally, such prior art converter circuits employ some sort of chopper, or oscillator, for effectively producing an AC signal, which signal may be amplified to a desired amplitude, following which it is rectified to re-establish the DC signal at the desired level. A large number of prior art designs are available, providing varying degrees of voltage amplification and regulation efficiency. However, all of these prior art circuits are designed with the assumption that the starting DC signal level is sufficient to enable unaided operation of the active device or devices being utilized. Power efficiency, or current drain in the converter unit, may or may not be a consideration in these circuits.

In spite of the prior art history of converter devices, there remain certain applications which require performance characteristics that have heretofore not been available. For example, in the field of cardiac pacing devices, referred to hereinafter as pacers, DC to DC converters are necessary where the power source provides a voltage which is too low to act as a supply for the logic and stimulus generating circuitry. In an extreme example, where nuclear powered sources are being utilized, the delivered voltage from the nuclear source is substantially less than 1 volt, and the available power is substantially less than one milliwatt. In such a case, conventional prior art converters are not able to provide the desired conversion, both because conventional designs don't provide the required oscillator startup characteristics and the converter efficiencies are too low to provide the required output power. A typical nuclear power source will have a voltage throughout its predicted lifetime which will vary between about 0.60 volts and 0.40 volts, with an internal impedance of about 100 to 300 ohms. In order to have an available voltage of 4 to 5 volts, and supply 20 to 25 ua, it is clear that a reasonably good converter efficiency is required. Also, particularly for an application such as a cardiac pacer, expense and reliability are important criteria, such that the simplest possible design is the best design.

For the nuclear power source characterized hereinabove, it is clear that at oscillator startup the starting current will be only a matter of several ma, even assuming zero input impedance at startup. Consequently, any active device, or devices, chosen for inclusion in the oscillator configuration must be characterized by having substantially negligible impedance when conductive, so as not to limit the starting current even further. The device also must be characterized by being switchable with a rather low voltage signal. It is known, of course, that oscillator startup may be achieved by designing high loop gain, but it is also understood that such overly high loop gain contributes to power loss and power inefficiency. Consequently, the application calls for a circuit design including a very low resistance starting current path and a configuration of one or more active devices providing a low switching level so that a relatively low loop gain oscillator can be employed. By selecting an active circuit configuration which presents an extremely low resistance when in the on state, and by utilizing a feedback circuit designed for efficient device operation, a highly power efficient oscillator is achieved which is capable of reliably starting when powered by an extremely low voltage level such as a nuclear power source. The addition of a low current drain stabilizer circuit which interfaces with the converter circuit provides means for efficiently and reliably delivering required power at a predetermined voltage.

SUMMARY OF THE INVENTION

It is the primary object of this invention to provide a DC to DC converter which overcomes the disadvantages of the prior art and, in particular, which provides for reliable and efficient DC to DC conversion of power sources characterized by voltage levels substantially less than 1 volt and a low current delivering capacity.

It is a further object of this invention to provide a DC to DC converter suitable for reliable operation when driven by a nuclear power source, the converter further being characterized by presenting a very low resistance starting path including a configuration of one or more active devices which can be switched efficiently, whereby the low value starting current supplied by the nuclear source causes switching in the converter, the switching being utilized for generating a higher voltage level output.

It is a further object of this invention to provide a configuration of active circuit devices characterized by having an extremely low resistance path when in its first state, and being further characterized by being switchable to a high resistance state in response to a relatively small voltage signal change at its control input terminal, the active device configuration being substantially independent of device selection and incorporated into a circuit driven by a very low voltage power source, for providing reliable switching as part of a DC to DC converter.

In accordance with the above objectives, there is provided an oscillator circuit adapted to be driven by a very low voltage, low current power source, a rectifier circuit for rectifying the AC output of the oscillator, and a regulator for regulating the rectified output at a desired DC level. The oscillator comprises either a single FET selected for its characteristics, or a pair of cascaded FET devices connected with their gates in common. The FET or the FET paid provide a very low level path when in the on state, as at oscillator startup, the FET pair also being characterized by having a low switching threshold.

BRIEF DESCRIPTION OF THE DRAWINGS

FIG. 1 is a circuit diagram of a first embodiment of the converter and stabilizer of this invention.

FIG. 2 is part circuit diagram and part block diagram, showing a second embodiment of this invention.

DESCRIPTION OF THE PREFERRED EMBODIMENTS

Referring now to FIG. 1, there is shown at the left hand side of the diagram a circuit representation of a typical power source. $V_{pr}$ represents the primary voltage source, or the open circuit voltage. For example, for a nuclear power source, this voltage may vary between about 0.4 volts to 0.6 volts. $R_{int}$ represents the internal resistance of the source, which may be in the range of 100 to 300 ohms. The source terminals 21 and 21' are connected to a converter device, which is indicated between vertical dashed lines. The output of the converter in turn is connected to a stabilizer, the stabilizer output being at terminals 22 and 22'. An effective load $R_1$ is shown in the diagram, and represents in the pacer application the rest of the implanted pacer.

Looking first at the converter circuit of FIG. 1, there is a capacitor C5 connected across terminals 21 and 21'. Terminal 21 is connected to the drain of FET 1, the source of which is connected to transformer coil 26. The gate of FET 1 is connected through resistor R6 to terminal 21', and to capacitor C4 which is also connected to one end of coil 26, the other end being connected to terminal 21. The junction between C4 and coil 26 is connected to a rectifier comprised of diode D2 and capacitor C6. Typical values of these components are as shown in the following table:

| COMPONENT | VALUE | |
| --- | --- | --- |
| C4 | 1.0 | μF |
| C5 | 3.3 | μF |
| C6 | 3.3 | μF |
| R6 | 20.0 | Megohm |

In practice, the drain to source resistance of an FET when on, as at the startup time, may be about 10 ohms. The pinch voltage $V_P$ of a typical FET may be in the range of 1 to 3 volts, or higher. At the time of startup, being the moment when the source is connected at terminals 21, 21' to the circuit, the current through FET 1 is limited primarily by the internal resistance of the source itself, so long as the selected FET has a low starting resistance. The startup current passes through a lower portion of coil 26. The coil has a turns ratio of 24:1, such that a feedback voltage is developed across the upper portion of coil 26 and coupled through capacitor C4 to the gate of FET 1. When the current through the lower portion of coil 26 increases, $V_{gs}$ increases and C4 is charged roughly to the voltage over coil 26 since the gate diode is forward biased. A decreasing current through the lower part of the coil causes a negative $V_{gs}$, cutting off the FET. Oscillation is started by the presence of noise, such that the turn-on resistance of the FET and the FET resistance variation with changes in $V_{gs}$ are important.

Resistor R6, connected between the gate of FET 1 and terminal 21', is preferably designed to place the oscillator in effective class C operation. Capacitor C4 charges up to a steady state voltage so as to hold the oscillator in class C operation, the FET being biased past cut off so that only at the peaks of the positive swing from the coil does the gate conduct. Capacitor C4 has built up across it a steady state bias voltage as indicated by the polarity designations on the drawing, in an amount greater than $V_P$ of the FET. For the component values as indicated in the Table, the steady state voltage across C4 is about 6 to 7 volts.

The regulator, or stabilizer portion of the circuit of FIG. 1 is driven by the rectified voltage which develops across C6. The stabilizer performs the function of providing a regulated DC voltage of a desired magnitude across terminals 22 — 22'. The regulator comprises an FET 2 connected between C6 and terminal 22. A regulating loop is comprised of a current source including FET 3 and resistor R4, and operational transconductance amplifier (OTA) 37. The output of OTA 37 drives the gate of FET 2, closing the control loop. A first input terminal of amplifier 37 is connected to the output of the current source, providing a reference voltage. The current source also provides the bias current to amplifier 37 through resistor R3, resistor R3 being shunted by capacitor C3. A signal representing the output voltage at terminal 22 is developed through the parallel combination of resistor R1 and capacitor C1, and connected to the negative terminal of amplifier 37. This terminal is also connected to output terminal 22' through the parallel combination of resistor R2 and capacitor C2. Resistor R5 is connected between capacitor C3 and resistor R2. A capacitor C7 is connected directly across terminals 22, 22', such that it shunts the load $R_1$. It is seen that a signal representing the difference between the reference voltage and the output voltage is developed in OTA 37, with the output current feedback providing regulation for stable operation.

The regulated output voltage may be trimmed to the desired voltage by adjusting resistor R4. The trimming procedure is carried out by loading the regulator circuit with a 1 megohm voltmeter parallel to capacitor C7, and connecting a 12 volt power supply across capacitor C6. The range of the trimming resistor R4 is suitably 1.7 megohm to 13 megohm, which range is acceptable provided that resistors R1, R2 and R3 match within 15% while the absolute tolerance does not exceed 30%.

By utilization of the current source, FETs and OTA in the configuration shown, there is provided a very low current drain stabilizer circuit such as has obvious advantages in applications such as cardiac pacers and the like. The stabilizer is, it is to be noted, useful with other forms of driving circuits and sources, and with other types of loads.

Referring now to FIG. 2, there is shown an alternate embodiment of a converter. The input terminals are connected across the power source, which is shown diagrammatically as having an ideal voltage source $V_{pr}$ and an internal resistance $R_{int}$, as in FIG. 1. The converter portion of FIG. 2 is the same as for FIG. 1, except that instead of one FET there is an FET pair 25 comprising two FETs 25' and 25" connected with their gates in common. The source of FET 25" is identified as node 31 and is the effective source of the FET pair; the drain of FET 25' is identified as node 30 and is the effective drain of the FET pair. By this connection, the FET pair provides an effective active device, or an active circuit, with characteristics which are uniquely desirable for low current starting operations. The two FET active circuit has a control terminal which is the common gate connection, and it provides a two state impedance characteristic.

The FETs when connected as a pair, in the manner shown, provide an effective more "ideal" FET characteristic. If a single ideal FET were available for this application, it would have a $V_P$ approaching zero volts, such that it would turn off when the slightest voltage is fed back through transformer 26. The addition, such an ideal FET would have an extremely low drain to source resistance when in the on state ($R_{DS-ON}$), as well as a reasonable gain. A wide variety of FET devices are available commercially, but as a practical matter a low $V_P$ FET cannot be found which also has a low $R_{DS\text{-}OB}$. The double FET arrangement as used herein provides an effectively lower $V_P$. The $V_P$ of each FET, of course, is not actually changed, but since the gain of the combination of the two cascaded FETs is higher, the result is as though the overall $V_P$ is lower. Additionally, the effective $R_{DS\text{-}ON}$ is substantially the combined series summation of the values of the two FET devices, and since this value for each FET can be very low, the overall value is quite low. Thus, the two FETs in combination act as though they were one effective FET having a drain connected at terminal 30, a source at terminal 31, and a gate connected to R6, the two FETs having a combined characteristic that is unobtainable with any single available FET.

In the preferred embodiment, FETs 25' and 25" are N channel depletion junction FETs. The N channel depletion junction FET gives a current flow at almost zero volts, so that the combination of two such devices in cascoded connection is extremely good for oscillator startup. In comparing the single FET and double FET circuits, tests made on a single FET of a given type showed a starting resistance of 10 ohms and a $V_P$ of 3 volts. For two FETs of the same type, the starting resistance was 20.9 ohms, and the overall $V_P$ was 2.45 volts. While the double FET circuit does not appear to provide any advantage in the normal current area of FET operation, it does give an improved result at starting, due to the improved overall $V_P$. A variety of FETs have been tested, and for some in the single FET circuit the source must be around 0.80 volts to initiate oscillation, while for the FET pair oscillation starts at around 0.27 volts. The FET pair is thus a more universal circuit which is less dependent upon FET selection, and thus a better design for guarding against the worst case. However, the double FET design, because of the increased "on" resistance, gives a slightly reduced output with a slightly increased power drain.

Referring now to both FIGS. 1 and 2, there is illustrated an improvement of the converter of this invention when utilized with a load device such as a cardiac pacer which is characterized by having an extremely low steady state power drain, and which periodically puts out a relatively high energy signal pulse. For example, in U.S. application Ser. No. 608,465, assigned to the same assignee, there is disclosed a cardiac pacer having a total current drain of about 3 uA, unloaded, and which periodically delivers a stimulus pulse which is limited to 10 milliamps. It can be understood that, for a load as constituted by such a pacer, regulation would be most critical during the period of the output stimulus pulse, the pulse width being normally about 1 millisecond. As seen in FIG. 2, the stabilizer output is connected to and provides power to an amplifier 41, a demand logic portion 42, and the oscillator 43. This is a basic configuration for what is referred to as a demand pacer, which type of pacer delivers output stimulus pulses as generated by the oscillator only in the absence of detected cardiac signals. As shown in FIG. 2, the output of the oscillator is connected to an electrode, or catheter 44, which is positioned within a patient's heart. The catheter is also connected back to the amplifier, which amplifies received cardiac signals which have been picked up by the catheter. Reference is made to the aforementioned application for a complete discussion of this type of cardiac pacing system. In such systems, the delivered output signal is a negative going stimulus pulse. In the improvement of this invention, the inverse of the oscillator output, being a positive going signal, is derived from the oscillator and fed back into the bias terminal of OTA 37, the feedback path including a current limiting resistor R12. See also FIG. 1. In this fashion, at precisely the moment when the pacing system is loading the power supply the greatest, a higher area open loop again back provided through the OTA control device, which provides extra regulation control during and only during the period of the output stimulus pulse. Since regulation is most critical at precisely the moment of the stimulus pulse output, this feedback circuit provides a decided additional advantage to the overall circuit operation.

While the preferred embodiments of the invention have been illustrated, it is to be noted that the invention is adaptable to be used with a wide range of sources and loads. For example, many types of low voltage level power sources are under development, and the converter of this invention may be adapted for use with many of them. In particular, the invention has advantages over the prior art for any application where there must be a low resistance path at time zero, i.e., at oscillator startup or when the source is initially placed or switched across the circuit. Also, the great efficiency of the circuit enables its use in certain applications where the power from the source is marginal in terms of the load demand. Likewise, the converter/stabilizer can drive many types of loads, such as other implantable medical electronic devices, communications systems, etc. The circuit has particular adaptability to any low power consumption operation wherein a low level source is utilized.

The basic plural FET configuration is adaptable to design variations, within the scope of this invention. Thus, just as 2 FETs can be combined into a pair as shown, 2 such pairs may be likewise combined. The plural FET configuration has applicability in any circuit where low level switching and high conductance in the "ON" state are desired.

While the preferred embodiment has been illustrated as used for converting the output of a power soure, the circuits of this invention are also generally useful in processing low level signals of whatever origin. It is to be noted that the double FET arrangement has application in switching circuits other than just in oscillators. For example, where an extremely low level supply must be utilized, and logic signals of low voltage and/or current must be processed, the circuit may be used primarily for its switching function. In the cardiac pacer application, the circuits of this invention can be driven by a battery which delivers much less than one milliwatt of power at a voltage in a range of 0.4 volts to 1 volt, and more likely a range of 0.4 volts to 0.6 volts. In a typical pacer application, a voltage of 4 to 7 volts would be delivered with an average current drain around 20 to 25 microamps.

We claim:
1. A circuit for DC to DC conversion of the voltage level of a low voltage power source, comprising:
   a. an oscillator circuit having an input for connection to said power source and an output for providing a relatively high amplitude oscillator signal, said oscillator circuit having a low starting resistance input path connected across said source, said path containing an active circuit comprised of at least two FETs, said active circuit being characterized by having a high impedance state and a low impedance state; and b. a rectifier circuit connected to said oscillator circuit output, for providing a rectified voltage signal from said oscillator signal.

2. The circuit as described in claim 1, comprising a regulator circuit with an input connected to said rectifier circuit and an output, said regulator circuit providing a regulated output from said rectified voltage signal.

3. The circuit as described in claim 1, wherein said active circuit comprises two FETs with their gates connected together.

4. The circuit as described in claim 1, wherein said FETs are both N channel junction FETs.

5. The circuit as described in claim 1, comprising said power source, and wherein said power source provides an output voltage between about 0.40 and 0.60 volts and delivers a maximum power of less than 1 milliwatt.

6. The circuit as described in claim 1, comprising a high resistance connected to said commonly connected gates.

7. The circuit as described in claim 1, in combination with power source means for providing less than 1 milliwatt of power with an output voltage less than 1 volt.

8. A circuit for conversion of the voltage level of a low voltage power source and for providing a regulated output, comprising:
 a. an oscillator circuit having an input for connection to said power source and an output for providing a relatively high amplitude oscillator signal, said oscillator circuit having a low starting resistance input path connected across said source, said path containing an active device, said device characterized by having a high impedance state and a low impedance state;
 b. a rectifier circuit connected to said oscillator output, for providing a rectified voltage signal from said oscillator signal;
 c. a regulator circuit with an output terminal, said regulator circuit connected to said rectifier circuit, for providing at said output terminal a regulated output from said rectified voltage signal, said regulator circuit comprising a regulating element between said rectifier circuit and said output terminal, and a regulating control path between said output terminal and said regulating element, said control path comprising an OTA, first input means for connecting to a first input terminal of said OTA a signal representative of said regulator output signal, said reference generator means being connected to a second input of said OTA, the output of said OTA being connected to said regulating element whereby said OTA acts to control said regulating element as a function of said output relative to said reference, said reference means comprising a current generator connected to said output terminal, the output of said current generator being connected both to said second OTA input terminal and into the OTA bias terminal, said current generator comprising an FET in combination with an adjustable resistor, whereby a regulated signal is provided at said regulator output terminal.

9. The circuit as described in claim 8, wherein said active device is an N channel FET.

10. The circuit as described in claim 9, wherein said oscillator circuit low starting resistance input path and the gain of said active device cooperate such that said oscillator starts when the voltage level supplied by said power source is greater than 0.4 volts and less than 0.6 volts.

11. The circuit as described in claim 9, comprising a high resistance connected to the gate of said FET.

12. The circuit as described in claim 8, wherein said power souce is characterized by having a maximum available power of less than a milliwatt, and the low impedance state of said active device cooperates with said power source such that said oscillator starts.

13. The circuit as described in claim 1, wherein said circuit is a portion of a cardiac pacer, said pacer comprising a stimulus generator for producing stimulus pulses, and further providing feedback means for connecting a feedback signal from said generator to the bias input terminal of said OTA, whereby the properties of said regulator circuit are affected by said feedback circuit upon the occurrence of an output stimulus pulse.

14. A circuit for conversion of the voltage level of a low voltage power source and for providing a regulated output, comprising:
 a. an oscillator circuit having an input for connection to said power source and an output for providing a relatively high amplitude oscillator signal, said oscillator circuit having a low starting resistance input path connected across said source, said path containing an active circuit comprised of at least two FETs, said active circuit being characterized by having a high impedance state and a low impedance state;
 b. a rectifier circuit connected to said oscillator output, for providing a rectified voltage signal from said oscillator signal;
 c. a regulator circuit with an output terminal, said regulator circuit connected to said rectifier circuit, for providing at said output terminal a regulated output from said rectified voltage signal, said regulator circuit comprising a regulating element between said rectifier circuit and said output terminal, and a regulating control path between said output terminal and said regulating element, said control path comprising an OTA, first input means for connecting to a first input terminal of said OTA a signal representative of said regulator output signal, reference generator means for generating a reference signal, said reference generator means being connected to a second input of said OTA, the output of said OTA being connected to said regulating element whereby said OTA acts to control said regulating element as a function of said output relative to said reference, whereby a regulated signal is provided at said regulator output terminal.

15. The circuit as described in claim 14, wherein said active circuit comprises two FETs with their gates connected together.

16. The circuit as described in claim 15, wherein said FETs are both N channel junction FETS.

17. The circuit as described in Claim 14, comprising said power source, and wherein said power source provides an output voltage between about 0.40 and 0.60 volts and delivers a maximum power of less than 1 milliwatt.

18. The circuit as described in claim 15, comprising a high resistance connected to said commonly connected gates.

19. The circuit as described in claim 14, wherein said reference means comprises a current generator connected to said output terminal, the output of said current generator being connected both to said second OTA input terminal and into the OTA bias terminal.

20. The circuit as described in claim 14, wherein said current generator comprises an FET in combination with an adjustable resistor.

21. The circuit as described in claim 14, wherein said power source is characterized by having a maximum available power of less than a milliwatt, and the low impedance state of said active device cooperates with said power source such that said oscillator starts.

22. The circuit as described in claim 14, wherein said circuit is a portion of a cardiac pacer, said pacer comprising a stimulus generator for producing stimulus pulses, and further providing feedback means for connecting a feedback signal from said generator to the bias input terminal of said OTA, whereby the properties of said regulator are affected by said feedback circuit upon the occurrence of an output stimulus pulse.

* * * * *

UNITED STATES PATENT OFFICE
CERTIFICATE OF CORRECTION

Patent No. 4,015,609  Dated April 5, 1977

Inventor(s) Cor A. Mensink and Jan P. Schuimer

It is certified that error appears in the above-identified patent and that said Letters Patent are hereby corrected as shown below:

Column 5, line 1, delete "$R_{DS-OB}$" and insert --$R_{DS-ON}$--.

Column 6, line 7, after "greatest," insert --there is--; same line, delete "area"; same line, delete "again back" and insert therefor --gain--.

Column 7, line 50, after "signal,", insert --reference generator means for generating a reference signal,--.

Signed and Sealed this fifth Day of July 1977

[SEAL]

Attest:

RUTH C. MASON  
Attesting Officer

C. MARSHALL DANN  
Commissioner of Patents and Trademarks